US00PP30728P2

(12) United States Plant Patent
Holtmaat

(10) Patent No.: US PP30,728 P2
(45) Date of Patent: Jul. 16, 2019

(54) ***RUDBECKIA* PLANT NAMED 'RUDHT25'**

(50) Latin Name: *Rudbeckia hirta*
Varietal Denomination: RUDHT25

(71) Applicant: Henricus Maria Joseph Holtmaat, Zuidwolde (NL)

(72) Inventor: Henricus Maria Joseph Holtmaat, Zuidwolde (NL)

(73) Assignee: Nova Perenne B.V., Zuidwolde (NL)

( * ) Notice: Subject to any disclaimer, the term of this patent is extended or adjusted under 35 U.S.C. 154(b) by 0 days.

(21) Appl. No.: 15/932,780

(22) Filed: Apr. 23, 2018

(51) Int. Cl.
*A01H 5/02* (2018.01)

(52) U.S. Cl.
USPC ..... Plt./474

(58) Field of Classification Search
USPC ..... Plt./263.1, 474
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Rudbeckia* plant named 'RUDHT25', characterized by its compact, broadly upright and mounded plant habit; freely branching growth habit; freely flowering habit; single-type inflorescences with yellow orange and greyed purple to brown bi-colored ray florets positioned above the foliar plane on strong peduncles; and good garden and container performance.

2 Drawing Sheets

Botanical designation: *Rudbeckia hirta.*
Cultivar denomination: 'RUDHT25'.

BACKGROUND OF THE INVENTION

The present invention relates to a new and distinct cultivar of *Rudbeckia* plant, botanically known as *Rudbeckia hirta*, commonly referred to as Black-eyed Susan, and hereinafter referred to by the name 'RUDHT25'.

The new *Rudbeckia* plant is a product of a planned breeding program conducted by the Inventor in Zuidwolde, The Netherlands. The objective of the breeding program is to create new compact *Rudbeckia* plants with numerous attractive inflorescences.

The new *Rudbeckia* plant originated from a cross-pollination made by the Inventor in Zuidwolde, The Netherlands in July, 2015 of two unnamed proprietary seedling selections of *Rudbeckia hirta*, not patented. The new *Rudbeckia* plant was discovered and selected by the Inventor as a single flowering plant from within the progeny of the stated cross-pollination in a controlled environment in Zuidwolde, The Netherlands in July, 2016.

Asexual reproduction of the new *Rudbeckia* by in vitro meristem culture in a controlled greenhouse environment in Zuidwolde, The Netherlands since March, 2017 has shown that the unique features of this new *Rudbeckia* are stable and reproduced true to type in successive generations.

SUMMARY OF THE INVENTION

Plants of the new *Rudbeckia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'RUDHT25'. These characteristics in combination distinguish 'RUDHT25' as a new and distinct *Rudbeckia* plant:

1. Compact, broadly upright and mounded plant habit.
2. Freely branching growth habit.
3. Freely flowering habit.
4. Single-type inflorescences with yellow orange and greyed purple to brown bi-colored ray florets positioned above the foliar plane on strong peduncles.
5. Good garden and container performance.

Plants of the new *Rudbeckia* differ from plants of the parent selections in the following characteristics in plant habit as plants of the new *Rudbeckia* are more compact and uniform than plants of the parent selections.

Plants of the new *Rudbeckia* can be compared to *Rudbeckia hirta* X *Echinacea purpurea* 'ET-RDB 02', disclosed in U.S. Plant Pat. No. 25,243. Plants of the new *Rudbeckia* differ primarily from plants of 'ET-RDB 02' in the following characteristics:

1. Plants of the new *Rudbeckia* are more compact than plants of 'ET-RDB 02'.
2. Plants of the new *Rudbeckia* and 'ET-RDB 02' differ in ray floret color as plants of 'ET-RDB 02' have yellow, orange and reddish-colored ray florets.

BRIEF DESCRIPTION OF THE PHOTOGRAPHS

The accompanying photographs illustrate the overall appearance of the new *Rudbeckia* showing the colors as true as it is reasonably possible to obtain in colored reproductions of this type. Colors in the photographs may differ slightly from the color values cited in the detailed botanical description which accurately describe the colors of the new *Rudbeckia.*

The photograph on the first sheet comprises a side perspective view of a typical flowering plant of 'RUDHT25' grown in a container.

The photograph at the top of the second sheet is a close-up view of a typical flowering plant of 'RUDHT25'.

The photograph at the bottom of the second sheet is a close-up view of typical leaves of 'RUDHT25'.

DETAILED BOTANICAL DESCRIPTION

The aforementioned photographs and following observations, measurements and values describe plants grown in 19-cm containers during the late summer and early autumn in an outdoor nursery in Zuidwolde, The Netherlands and under cultural conditions typical of commercial *Rudbeckia* production. During the production of the plants, day temperatures ranged from 18° C. to 30° C. and night temperatures ranged from 6° C. to 18° C. Plants were 18 weeks old when the photographs were taken and 17 weeks old when the detailed description was taken. In the following description, color references are made to The Royal Horticultural Society Colour Chart, 2015 Edition, except where general terms of ordinary dictionary significance are used.

Botanical classification: *Rudbeckia hirta* 'RUDHT25'.

Parentage:

*Female, or seed, parent*.—Unnamed proprietary seedling selection of *Rudbeckia hirta*, not patented.

*Male, or pollen, parent*.—Unnamed proprietary seedling selection of *Rudbeckia hirta*, not patented.

Propagation:

*Type*.—By in vitro meristem culture.

*Time to initiate roots*.—About ten days at soil temperatures about 15° C. and ambient temperatures about 20° C.

*Time to produce a rooted young plants*.—About 30 to 35 days at soil temperatures about 15° C. and ambient temperatures about 20° C.

*Root description*.—Medium in thickness; fleshy; typically white in color, actual color of the roots is dependent on substrate composition, water quality, fertilizers, substrate temperature and physiological age of roots.

*Rooting habit*.—Freely branching; medium density.

Plant description:

*Plant and growth habit*.—Herbaceous perennial; compact, broadly upright and mounded plant habit; strong and freely branching growth habit with about six primary lateral branches each with about six secondary lateral branches; dense and bushy appearance; moderately vigorous to vigorous growth habit; medium to rapid growth rate.

*Plant height*.—About 54.2 cm.

*Plant width*.—About 50.3 cm.

*Lateral branches*.—Length: About 24.4 cm. Diameter: About 4 mm. Internode length: About 4.3 cm. Angle: Primary lateral branches are upright to about 40° from vertical and secondary lateral branches are about 20° from primary lateral branches axis. Strength: Moderately strong. Texture and luster: Densely pubescent; moderately glossy. Lenticels: None observed on plants of the new *Rudbeckia*. Color: Developing branches, close to 144B; developed branches, close to 144B with axillary stripes, close to 143A, and at the nodes, close to 144B.

Leaf description:

*Arrangement*.—Alternate, simple; sessile.

*Length*.—About 9.2 cm.

*Width*.—About 4.7 cm.

*Shape*.—Obovate to elliptic.

*Apex*.—Acute.

*Base*.—Truncate to cuneate.

*Margin*.—Coarsely and shallowly serrate.

*Texture and luster, upper and lower surfaces*.—Pubescent, rough; matte.

*Venation pattern*.—Pinnate.

*Color*.—Developing leaves, upper surface: Close to 143A. Developing leaves, lower surface: Close to between 143B and 146C. Fully expanded leaves, upper surface: Close to 137B; venation, close to 145C to 145D. Fully expanded leaves, lower surface: Close to 146B; venation, close to 144C.

Inflorescence description:

*Type and arrangement*.—Single-type inflorescence form with obovate-shaped ray florets and tubular disc florets; inflorescences borne on terminal and axillary peduncles above and beyond the foliar plane on strong peduncles; ray and disc florets arranged acropetally on a capitulum.

*Fragrance*.—None detected.

*Flowering season*.—Plants begin flowering about 100 days after planting; long flowering period, plants flower continuously during the late summer to late autumn in The Netherlands.

*Inflorescence longevity*.—Good postproduction longevity with inflorescences lasting about two to five weeks on the plant; inflorescences not persistent.

*Quantity of inflorescences*.—Freely flowering habit, typically about 36 developing and fully developed inflorescences at one time.

*Inflorescence buds*.—Height: About 2.2 cm. Diameter: About 2.8 cm. Shape: Broadly ovate. Texture and luster: Densely pubescent; matte. Color: Close to between 15B and 16A.

*Inflorescences*.—Diameter: About 9.6 cm. Depth (height): About 4.7 cm. Diameter of disc: About 2.6 cm. Receptacle height: About 1.3 cm. Receptacle diameter: About 1.1 cm. Receptacle shape: Ovate. Receptacle color: Close to 157A.

*Ray florets*.—Quantity and arrangement: About 30 per inflorescence arranged in about two whorls. Length: About 4.4 cm. Width: About 1.8 cm. Shape: Obovate. Apex: Emarginate to praemorse. Base: Cuneate. Margin: Entire. Aspect: When developing, upright and when fully opened, outward to slightly drooping. Texture and luster, upper surface: Smooth, glabrous; velvety; matte. Texture and luster, lower surface: Densely pubescent; slightly velvety; matte. Color: When opening, upper surface: Distally, close to 17B; proximally, close to between N186C and 200A. When opening, lower surface: Distally, close to 17B; proximally, close to 152D. Fully opened, upper surface: Distally, close to 17B; proximally, close to between N186C and 200A. Fully opened, lower surface: Distally, close to 17B; proximally, close to 153C.

*Disc florets*.—Quantity and arrangement: About 700 per inflorescence arranged in a spiral of about 14 whorls. Length: About 1.1 cm. Width: About 4 mm. Shape: Lower 89% fused and tubular, elongated. Apex: Acute. Aspect: Upright. Texture and luster: Smooth, glabrous; glossy. Color: When opening, inner and outer surfaces: Distally, close to between N186C and 200A; proximally, close to 155A. Fully opened, inner and outer surfaces: Distally, close to between N186C and 200A; mid-section, close to 185C; proximally, close to 155A.

*Phyllaries*.—Quantity and arrangement: About 28 per inflorescence arranged in about two whorls. Length: About 2.5 cm. Width: About 7 mm. Shape: Narrowly obovate. Apex: Acute. Base: Broadly cuneate. Margin: Entire. Texture and luster, upper and lower surfaces: Densely pubescent; matte. Color, upper surface: Close to 137C. Color, lower surface: Close to 143B.

*Peduncles*.—Length: About 16.1 cm. Diameter: About 4 mm. Strength: Strong. Aspect: Mostly upright. Texture and luster: Densely pubescent; moderately glossy. Color: Close to 144B with axillary stripes, close to 143A.

*Reproductive organs*.—Androecium (present only on disc florets): Quantity per disc floret: About five. Filament length: About 3 mm. Filament color: Close to 155A. Anther shape: Narrowly oblong. Anther length: About 3 mm. Anther width: About 0.5 mm. Anther color: Close to 200A. Pollen amount: Scarce. Pollen color: Close to 17A. Gynoecium (present only on disc florets): Pistil length: About 8 mm. Style length: About 5 mm. Style color: Close to 155A. Stigma diameter: About 3 mm. Stigma shape: Cleft, decurrent. Stigma color: Close to between 200A and 202A. Ovary color: Close to NN155B.

*Seeds and fruits*.—Seed and fruit production has not been observed on plants of the new *Rudbeckia* to date.

Disease & pest resistance: Plants of the new *Rudbeckia* have not been observed to be resistant to pathogens and pests common to *Rudbeckia* plants.

Garden performance: Plants of the new *Rudbeckia* have been observed to have good garden performance and to tolerate wind, rain, high temperatures about 35° C. and to be suitable for USDA Hardiness Zones 5 to 10.

It is claimed:

1. A new and distinct *Rudbeckia* plant named 'RUDHT25' as illustrated and described.

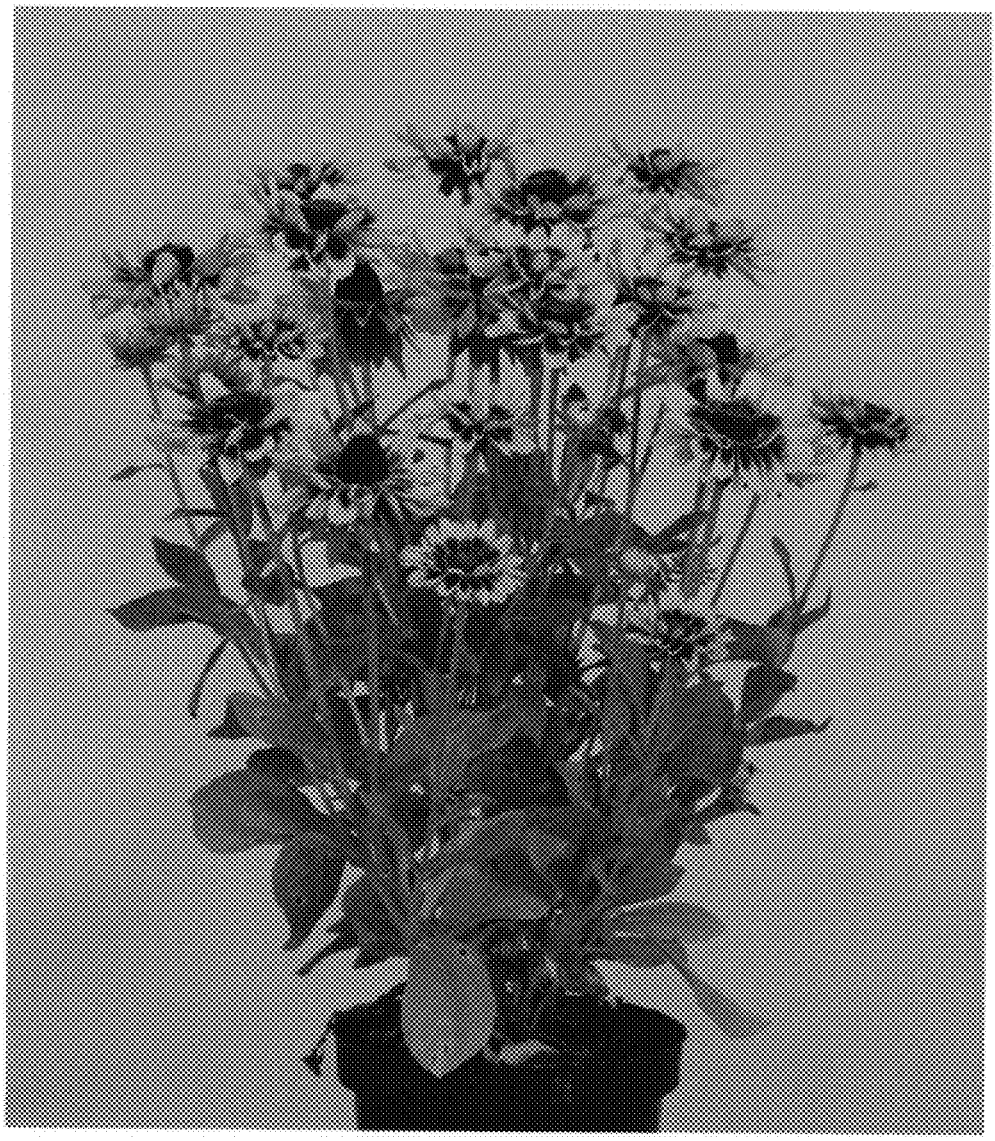

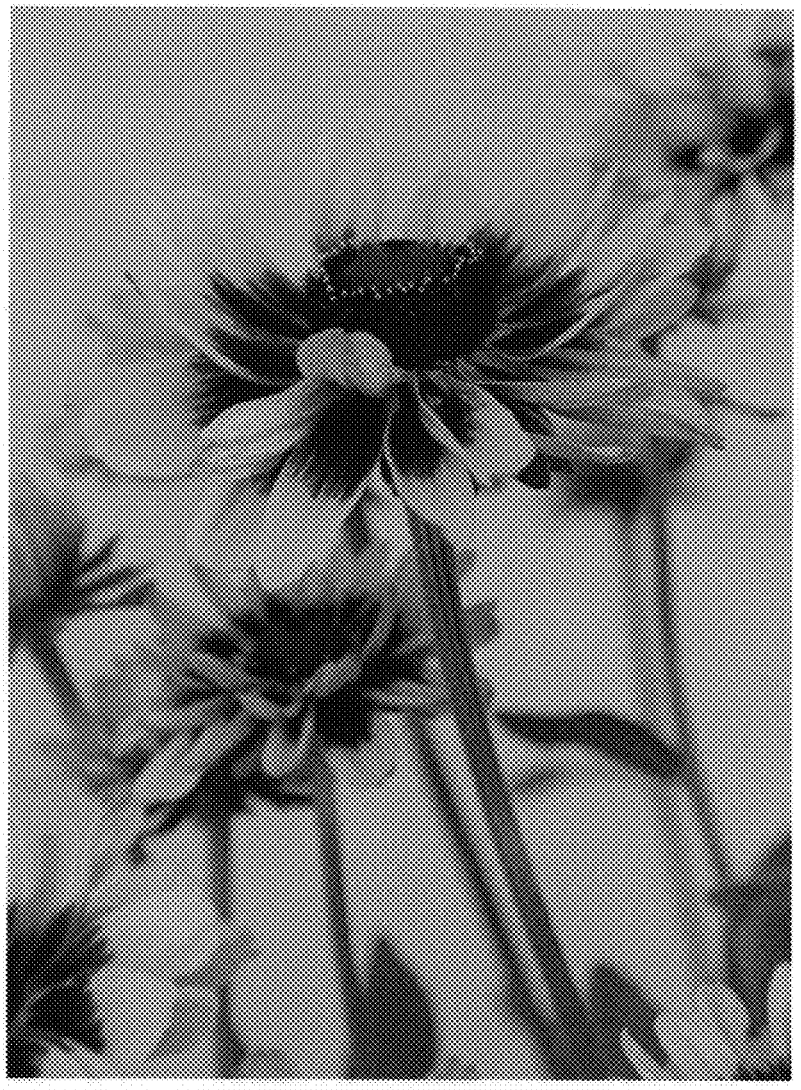
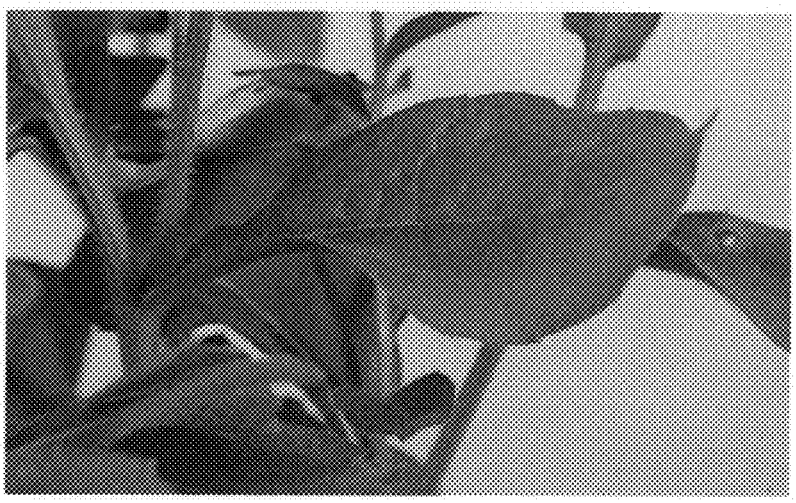

* * * * *